(12) United States Patent
Ben Shoshan et al.

(10) Patent No.: US 10,859,488 B2
(45) Date of Patent: Dec. 8, 2020

(54) SAMPLE HOLDER FOR HOME TESTING DEVICE

(71) Applicant: MES MEDICAL ELECTRONIC SYSTEMS LTD., Caesarea (IL)

(72) Inventors: Assaf Ben Shoshan, Kibbutz Barkai (IL); Lior Shriki, Haifa (IL); Marcia Deutsch, Los Angeles, CA (US)

(73) Assignee: MES MEDICAL ELECTRONIC SYSTEMS LTD., Caesarea (IL)

( * ) Notice: Subject to any disclaimer, the term of this patent is extended or adjusted under 35 U.S.C. 154(b) by 0 days.

(21) Appl. No.: 16/379,851

(22) Filed: Apr. 10, 2019

(65) Prior Publication Data

US 2019/0234864 A1 Aug. 1, 2019

Related U.S. Application Data

(62) Division of application No. 15/037,050, filed as application No. PCT/IB2014/066716 on Dec. 9, 2014, now abandoned.

(60) Provisional application No. 61/914,980, filed on Dec. 12, 2013.

(51) Int. Cl.
| | |
|---|---|
| *G01N 15/14* | (2006.01) |
| *G01N 15/06* | (2006.01) |
| *G01N 15/10* | (2006.01) |
| *G06K 9/00* | (2006.01) |
| *C12M 3/00* | (2006.01) |
| *C12M 1/00* | (2006.01) |
| *C12M 1/34* | (2006.01) |
| *H04M 1/725* | (2006.01) |
| *H04B 1/3888* | (2015.01) |

(Continued)

(52) U.S. Cl.
CPC ......... *G01N 15/1463* (2013.01); *C12M 21/06* (2013.01); *C12M 23/22* (2013.01); *C12M 41/36* (2013.01); *G01N 15/06* (2013.01); *G01N 15/0606* (2013.01); *G06K 9/00134* (2013.01); *H04B 1/3888* (2013.01); *H04M 1/0264* (2013.01); *H04M 1/72527* (2013.01); *H04N 5/2254* (2013.01); *H04N 5/2256* (2013.01); *G01N 2015/0693* (2013.01); *G01N 2015/1006* (2013.01); *G01N 2015/1075* (2013.01); *G01N 2015/1486* (2013.01)

(58) Field of Classification Search
None
See application file for complete search history.

(56) References Cited

U.S. PATENT DOCUMENTS

| | | | |
|---|---|---|---|
| 3,638,188 A | 1/1972 | Pincoffs et al. | |
| 3,829,216 A * | 8/1974 | Persidsky | G02B 21/34 356/36 |

(Continued)

OTHER PUBLICATIONS

U.S. Appl. No. 16/438,484 office action dated Dec. 31, 2019.

*Primary Examiner* — Shawn Decenzo
*Assistant Examiner* — Jarreas C Underwood
(74) *Attorney, Agent, or Firm* — Fresh IP PLC; Clifford D. Hyra; Aubrey Y Chen (57) ABSTRACT

A sample holder includes a slide, containing a depression in a surface of the slide. A cover slip is fixed to the slide over the depression so as to define a sample chamber, while leaving a loading area of the depression uncovered, so that a liquid sample deposited in the loading area is drawn into the sample chamber by capillary action.

9 Claims, 6 Drawing Sheets

(51) Int. Cl.
*H04M 1/02* (2006.01)
*H04N 5/225* (2006.01)

(56) References Cited

U.S. PATENT DOCUMENTS

| | | | |
|---|---|---|---|
| 4,171,866 A * | 10/1979 | Tolles | G02B 21/34 |
| | | | 356/244 |
| 4,790,640 A * | 12/1988 | Nason | B01L 3/502707 |
| | | | 156/99 |
| 4,804,600 A * | 2/1989 | Kato | G03F 1/22 |
| | | | 378/34 |
| 4,908,872 A | 3/1990 | Toriu et al. | |
| 6,052,224 A * | 4/2000 | Richardson | B01L 3/508 |
| | | | 359/398 |
| 6,173,077 B1 | 1/2001 | Trew et al. | |
| 6,272,233 B1 | 8/2001 | Takeo | |
| 7,081,940 B2 * | 7/2006 | Suzuki | G02F 1/1339 |
| | | | 349/153 |
| 7,279,063 B2 * | 10/2007 | Yokajty | H01L 51/5246 |
| | | | 156/275.5 |
| 7,718,124 B2 * | 5/2010 | Simmet | B01L 3/502715 |
| | | | 422/547 |
| 9,784,961 B2 * | 10/2017 | Wooder | G02B 21/0004 |
| 2002/0114577 A1 * | 8/2002 | Kondo | G02B 6/423 |
| | | | 385/51 |
| 2003/0031366 A1 | 2/2003 | Li et al. | |
| 2006/0067187 A1 * | 3/2006 | Yang | G11B 7/26 |
| | | | 369/47.11 |
| 2007/0298454 A1 | 12/2007 | Green et al. | |
| 2009/0238423 A1 | 9/2009 | Rigler | |
| 2013/0163844 A1 | 6/2013 | Ozaki et al. | |
| 2013/0314526 A1 | 11/2013 | Yasuda et al. | |
| 2014/0212959 A1 * | 7/2014 | Matsuura | G01N 15/1463 |
| | | | 435/288.7 |
| 2014/0267670 A1 * | 9/2014 | Tipgunlakant | G02B 21/16 |
| | | | 348/79 |
| 2014/0356864 A1 * | 12/2014 | Khan | G01N 21/25 |
| | | | 435/5 |
| 2016/0147056 A1 * | 5/2016 | Corwin | G02B 27/32 |
| | | | 359/391 |
| 2016/0211166 A1 * | 7/2016 | Yan | H01J 37/023 |
| 2018/0250670 A1 * | 9/2018 | Le Berre | B01L 3/5088 |

\* cited by examiner

SAMPLE HOLDER FOR HOME TESTING DEVICE

CROSS-REFERENCE TO RELATED APPLICATIONS

This application is a division of U.S. patent application Ser. No. 15/037,050, filed May 17, 2016, in the national phase of PCT Patent Application PCT/IB2014/066716, filed Dec. 9, 2014, which claims the benefit of U.S. Provisional Patent Application 61/914,980, filed Dec. 12, 2013, which is incorporated herein by reference.

FIELD OF THE INVENTION

The present invention relates generally to optical inspection of samples, and specifically to automated methods and devices for capture and analysis of electronic images of samples.

BACKGROUND

Infertility is a common yet complex problem, affecting approximately 10-15% of couples attempting to conceive a child. In up to one third of these cases, the problem is at least in part related to male reproductive issues. Among these issues, low sperm motility is commonly associated with infertility. A qualitative assessment of motile sperm can be made by visually evaluating the motion of the sperm in the sample under the microscope. These microscope systems are generally expensive, however, and are not suitable for use by inexperienced personnel. This sort of visual evaluation can produce inconsistent results even when used by well-trained personnel.

A number of devices and methods have been developed for automated sperm motility testing. For example, U.S. Patent Application Publication 2014/0254004 describes test kits for assessing male fertility, which include a sample holder defining an object plane, a lens, and a two-dimensional light sensor defining an image plane arranged along a common linear axis. The test kit may have a housing with a maximum linear dimension of no more than 100 mm Processing circuitry may be provided that is configured to produce a sperm count and/or sperm motility measurements by processing image data from the two-dimensional light sensor.

Nearly all mobile telephones currently on sale include built-in cameras, which may be used in various applications. For example, U.S. Patent Application Publication 2011/0292198 describes a microscope accessory for attachment to a mobile phone having a display positioned in a first face and a camera positioned in an opposite second face. The microscope accessory includes engagement features for releasably attaching the microscope accessory to the mobile phone, and an optical assembly having a first mirror positioned to be offset from the camera, a second mirror positioned for alignment with the camera, and a microscope lens positioned in the optical path. The optical assembly is matched with the camera, such that a surface is in focus when the mobile phone lies flat against the surface.

SUMMARY

Some of the embodiments of the present invention that are described hereinbelow provide devices and methods that make use of the imaging and processing capabilities of a mobile computing device, such as a Smartphone, to perform microscopic inspection and automated assessment of a sample.

There is therefore provided, in accordance with an embodiment of the present invention, an optical device, including a case, which is configured to fit over at least a part of a mobile computing device having first and second faces and including a light source, which emits a beam of illumination through an exit aperture, and a camera module, which captures images through an entrance aperture, wherein both the entrance and exit apertures open through the second face of the mobile computing device. A receptacle in the case is configured to receive and position a sample in proximity to the second face of the mobile computing device within a field of view of the camera module. Illumination optics are configured to receive and turn the beam emitted by the light source so as to back-illuminate the sample while the camera module captures one or more images of the back-illuminated sample.

In the disclosed embodiments, the light source directs the beam away from the second face of the mobile computing device, and the illumination optics include at least one reflector, which is configured to reflect the beam back toward the second face. The device may include a pair of reflective surfaces, each configured to turn the beam by 90°.

In some embodiments, the device includes a lens mounted in the case in a location between the sample and the entrance aperture and configured so that the sample is located within a focal range of the camera module. Typically, the lens is configured to magnify the one or more images captured by the camera module. In a disclosed embodiment, the lens includes a ball lens, having wings attached thereto for mounting in the case.

In some embodiments, the apparatus includes a transparent sample holder, which is configured to receive the sample and to be positioned within the receptacle so as to position the sample securely in the field of view of the camera. When the sample is liquid, the sample holder typically includes a slide having a depression formed therein to contain the sample and a cover slip fixed over the depression.

There is also provided, in accordance with an embodiment of the present invention, testing apparatus, including a mobile computing device having first and second faces and including a light source, which emits a beam of illumination through an exit aperture, and a camera module, which captures images through an entrance aperture, wherein both the entrance and exit apertures open through the second face of the mobile computing device. The apparatus further includes an optical device as described above, which is configured to fit over the mobile computing device so that the receptacle positions the sample within the field of view of the camera module, and the illumination optics are aligned with the light source.

In a disclosed embodiment, the mobile computing device is a Smartphone.

Typically, the mobile computing device includes a processor, which is configured to process the captured images so as to analyze a property of the sample. In some embodiments, the sample includes semen, and the processor is configured to analyze a motility characteristic of spermatozoa in the semen.

Additionally or alternatively, the mobile computing device includes a display screen on the first face of the mobile computing device, and the processor is configured to present an assessment of the property on the display screen.

There is additionally provided, in accordance with an embodiment of the present invention, a sample holder, including a slide, containing a depression in a surface of the slide, and a cover slip, which is fixed to the slide over the depression so as to define a sample chamber, while leaving a loading area of the depression uncovered, so that a liquid sample deposited in the loading area is drawn into the sample chamber by capillary action.

In a disclosed embodiment, the slide is molded to define at least one first groove, into which an adhesive is inserted in order to fix the cover slip to the slide, and at least one second groove located between the at least one first groove and the depression so as to prevent overflow of the adhesive from the at least one first groove into the sample chamber.

There is further provided, in accordance with an embodiment of the present invention, a method for testing, which includes inserting a sample into a transparent sample holder and inserting the transparent sample holder with the sample into an optical adapter. The optical adapter is fitted over a mobile computing device that includes a light source, which emits a beam of illumination through an exit aperture, and a camera module, which captures images through an entrance aperture, so that the sample is positioned within a field of view of the camera module. An image of the sample in the optical adapter is captured using the camera module while illuminating the sample with the beam emitted by the light source. The captured image is analyzed in the mobile computing device so as to compute and output an assessment of the sample.

In some embodiments, the sample is liquid, and the sample holder includes a slide having a depression formed therein to contain the sample and a cover slip fixed over the depression. In a disclosed embodiment, the cover slip is fixed to the slide over the depression so as to define a sample chamber, while leaving a loading area of the depression uncovered, and inserting the sample includes depositing the sample in the loading area so that the liquid is drawn into the sample chamber by capillary action.

In a disclosed embodiment, the mobile computing device is a Smartphone, and analyzing the captured image includes processing the captured image using application software running on a processor in the Smartphone.

In some embodiments, the sample includes semen, and analyzing the captured image includes assessing a motility characteristic of spermatozoa in the semen, for example by computing a motile sperm concentration.

The present invention will be more fully understood from the following detailed description of the embodiments thereof, taken together with the drawings in which:

DETAILED DESCRIPTION OF EMBODIMENTS

In view of the high incidence of male fertility problems, sperm testing should be performed at an early stage in most cases in which a couple has difficulty in conceiving. Such testing requires, however, that the man either ejaculate a semen sample at the laboratory, which can be difficult and embarrassing, or rush the sample from his home to the laboratory, with the risk that the sperm may die in transit.

Embodiments of the present invention that are described herein address this problem by providing an automated sperm testing apparatus that can be operated conveniently and reliably in the privacy of one's home. The apparatus comprises an optical adapter, which fits onto an existing mobile computing device, such as a smart phone, and converts the device into a video microscope. The apparatus takes advantage of the existing resources of the mobile computing device, including camera (and its internal optics), illumination source, processor and display screen, and thus provides a low-cost solution that enables the user to test his semen at home at any stage, even before going to see a doctor.

In the disclosed embodiments, a clip-on optical adapter device comprises a case, which fits over at least the part of a mobile computing device, such as a Smartphone, where the light source and camera module are located. The case of the adapter device has a receptacle for a sample, such as a semen sample or other liquid sample, contained in a suitable sample holder, such as a transparent slide. When inserted into this receptacle, the sample is positioned within the field of view and focal range of the camera module, in proximity to the face of the mobile computing device where the entrance and exit apertures are located. In the disclosed embodiments, the desired focus and magnification of the sample are achieved with the assistance of internal optics in the adapter device, as described below.

To capture a suitable electronic image of the sample for analysis, it is desirable that the sample be back-illuminated. In all common Smartphones, as well as other, similar devices, however, the exit aperture of the light source and the entrance aperture of the camera module are located on the same face of the device, not facing one another as required for back-illumination. A separate light source could be provided for this purpose, but this approach increases the size and cost of the adapter and also requires it to provide power to the light source.

Instead, the disclosed embodiments of the present invention exploit the existing light source in the mobile computing device itself, using illumination optics in the case of the adapter device to receive and turn the beam emitted by the light source so as to back-illuminate the sample. Thus, the camera module (with the assistance of the optics in the adapter device) captures back-illuminated images of the sample, which are processed by the mobile computing device in order to compute and output an assessment of the sample. Typically, the adapter device also comprises a lens mounted in the case in a location between the sample and the entrance aperture of the camera module, which magnifies the images captured by the camera module.

A clip-on adapter of this sort, which takes advantage of the light source and camera module in a Smartphone or other mobile computing device, can be useful in various methods for automated testing. Thus, embodiments of the present invention also provide a method in which a sample is inserted into a transparent sample holder, the transparent sample holder with the sample is inserted into an optical adapter, and the optical adapter is fitted over a mobile computing device. (Alternatively, the adapter may first be fitted over the mobile computing device, after which the sample holder is inserted into the adapter.) The camera module captures one or more electronic images of the sample, which is illuminated by the beam emitted by the light source in the Smartphone. An application program running on the mobile computing device actuates the light source and camera module, and causes the processor in the device to analyze the images so as to compute and output an assessment of the sample.

In a disclosed embodiment, the sample comprises semen, as noted above, and the processor assesses the motility of the spermatozoa in the semen. Advantageously, the processor may compute and output an assessment of a motility characteristic of the spermatozoa, such as the motile sperm concentration(MSC, also referred to in some publications as motile sperm count), which is the product of the sperm concentration multiplied by the percent motility of the sperm (divided by 100). Because MSC integrates these two parameters, it gives a better screening indication for fertility problems than either sperm concentration or motility alone.

Figure 1:
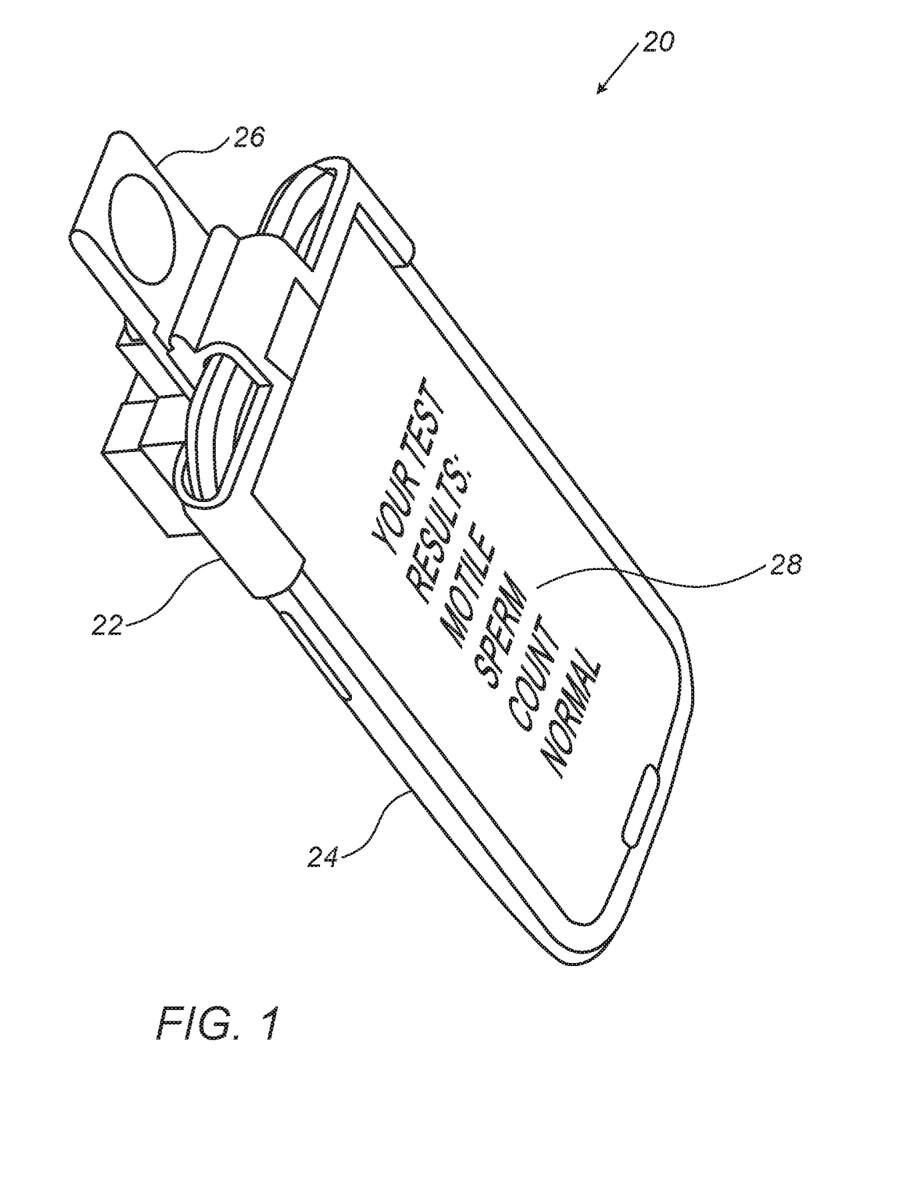
FIG. 1 is a schematic, pictorial illustration of testing apparatus, in accordance with an embodiment of the present invention.

FIG. 1 is a schematic, pictorial illustration of testing apparatus 20, in accordance with an embodiment of the present invention. Apparatus 20 comprises a mobile computing device in the form of a Smartphone 24, which may be of any suitable type that is known in the art. An optical adapter device 22 fits over the upper part of Smartphone 24. A sample holder, in the form of a test slide 26, is inserted into the adapter device, so that the sample that it contains is positioned within the field of view and focal range of the camera module in Smartphone 24 (as shown in the figures that follow, which include the internal optics in adapter device 22).

The processor (not shown) in Smartphone 24 analyzes images captured by the camera module in order to make an assessment of the sample, and outputs the assessment to a display screen 28. The images captured by the camera module are referred to interchangeably herein as "electronic images" or "video images." For the sake of clarity in the description that follows, the term "first face" in reference to Smartphone 24 refers to the side of the Smartphone on which display screen 28 is located, while the reverse face, facing into the page in FIG. 1, is referred to as the second face.

Although the present embodiment and the figures in this patent application refer to a particular type of Smartphone, the features of this embodiment may be adapted, mutatis mutandis, to work with Smartphones of other types and designs, as well as with other mobile devices having suitable imaging and computing capabilities, such as tablet and laptop computers. All such alternative implementations are considered to be within the scope of the present invention.

Figures 2A, 2B:
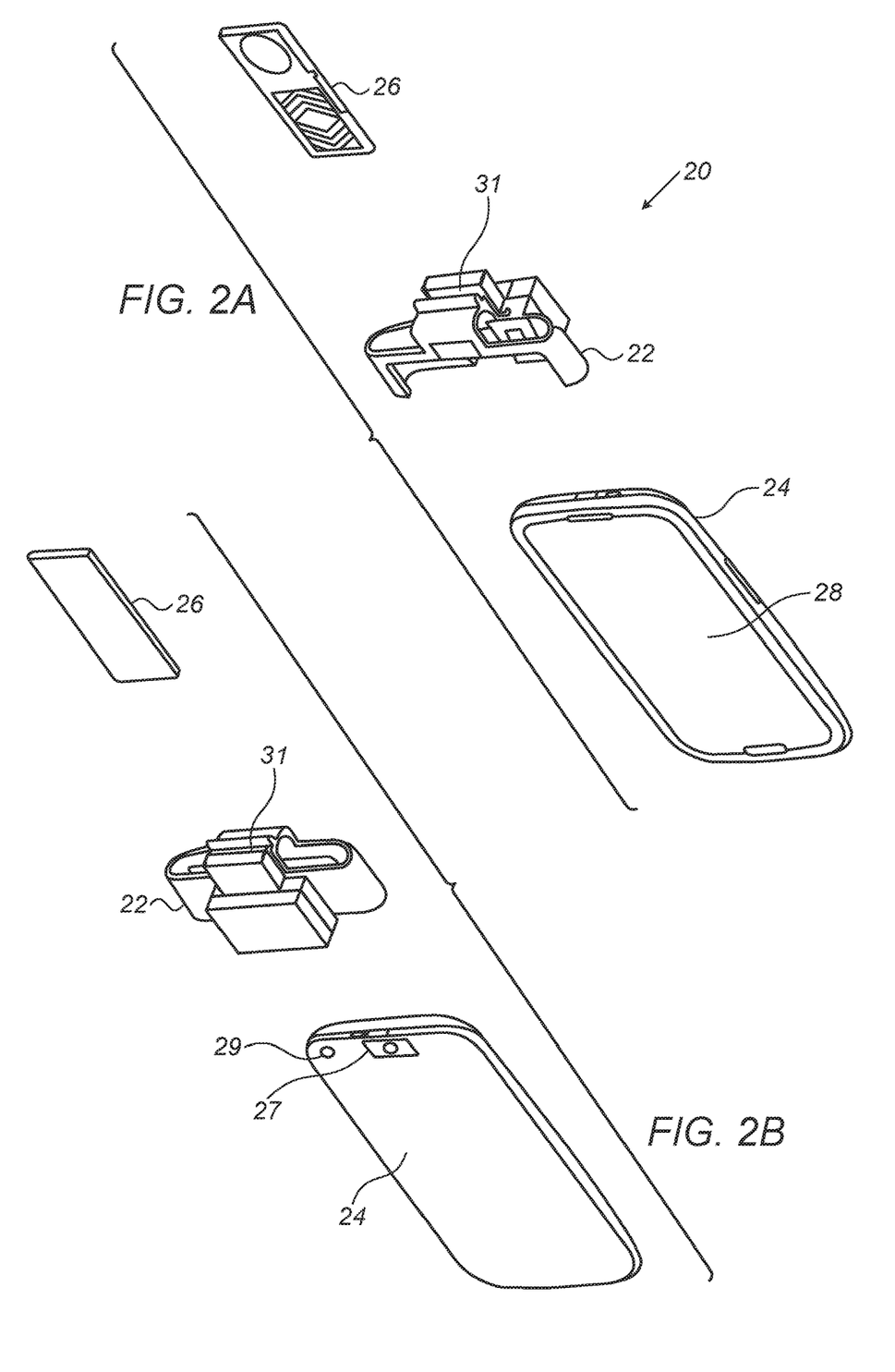
FIGS. 2A and 2B are schematic exploded views of the apparatus of FIG. 1, shown from the front and rear sides of the apparatus, respectively, in accordance with an embodiment of the present invention.

FIGS. 2A and 2B are schematic exploded views of apparatus 20, shown from the front and rear sides, respectively, in accordance with an embodiment of the present invention. As noted earlier, FIG. 2A shows the "first face" of Smartphone 24, while FIG. 2B shows the "second face." The Smartphone comprises a camera module 27 and a light source 29, which respectively have an entrance aperture and an exit aperture alongside one another in the second face of the Smartphone. Adapter device 22 fits over the end of Smartphone 24 and covers the entrance and exist apertures of camera module 27 and light source 29.

Test slide 26 fits into a receptacle 31, which is shaped as a slot in the case of adapter device 22. Alternatively, receptacle 31 may be configured to receive samples and sample holders, made of appropriate transparent materials, of any suitable size and shape.

Figure 3:
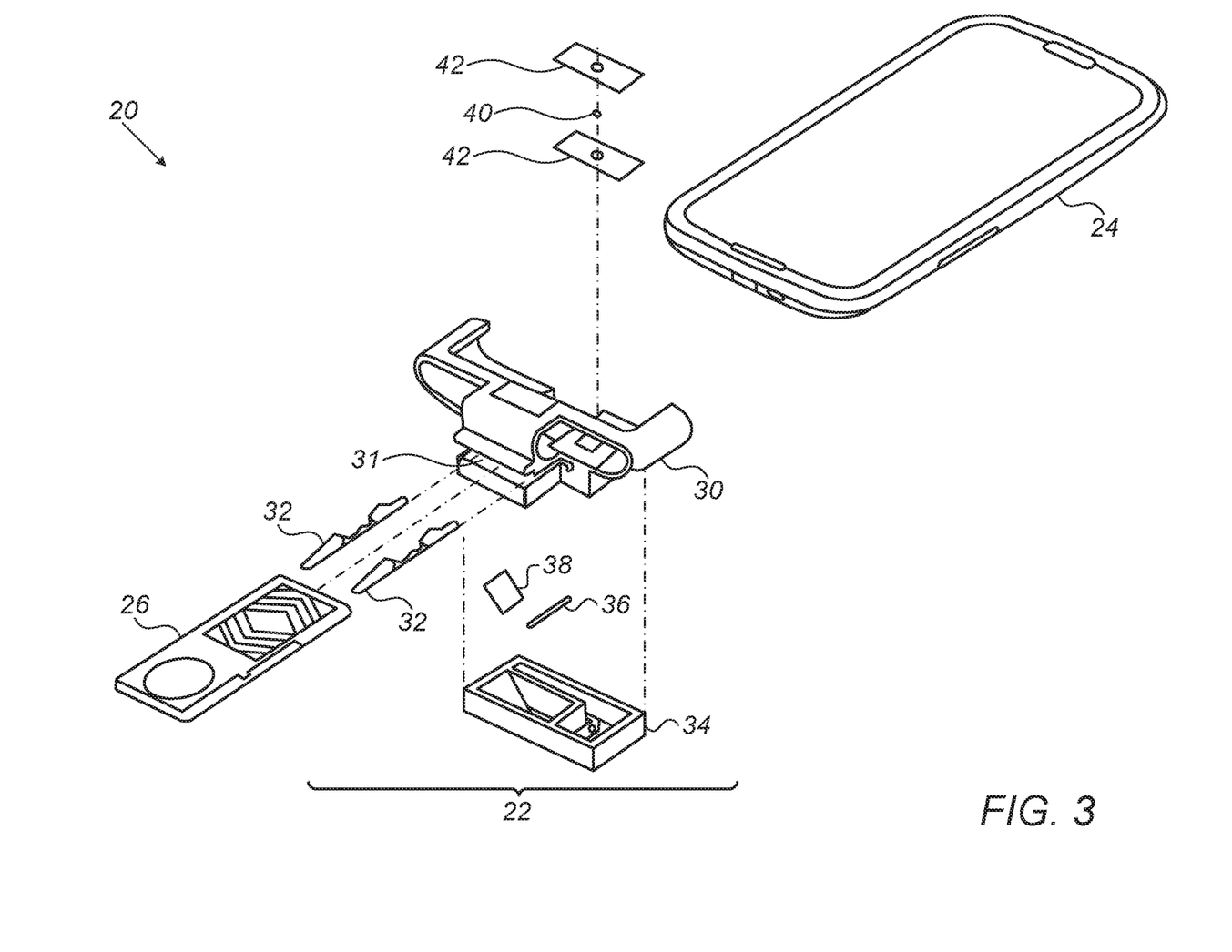
FIG. 3 is a schematic exploded view of a microscopy adapter for a mobile computing device used in the apparatus of FIG. 1, in accordance with an embodiment of the present invention.

FIG. 3 is a schematic exploded view of adapter device 22, in accordance with an embodiment of the present invention. Device 22 comprises a case 30, which is typically made from molded plastic and includes a slot for receptacle 31. Springs 32 are fitted into the case in order to hold slide 26 securely and precisely in the receptacle, with the sample in the field of view and focal range of camera module 27. A mirror holder 34 fits onto the back of case 30 and holds a pair of mirrors 36 and 38, whose operation as illumination optics in device 22 is described below with reference to FIG. 4.

A ball lens 40, held between a pair of lens holders 42, is mounted in case 30 in a location between the sample held by slide 26 and the entrance aperture of camera module 27. Springs 32 hold slide 26 at a fixed, accurate distance from lens 40. Lens 40 serves to magnify the images of the sample that are captured by the camera module. Lens holders 42 are shaped as wings, extending out to either side of ball lens 40, without occluding the small optical aperture of the ball lens. Alternatively, the ball lens and wings may be molded together out of a single piece of optical plastic or glass. Typically, ball lens 40 is about 2 mm in diameter, although larger or smaller elements may alternatively be used. Further alternatively, ball lens 40 may be replaced by other magnifying optics, such as a miniature simple lens (either spherical or aspheric) or even a compound lens, depending on the desired magnification and other optical requirements.

Figure 4:
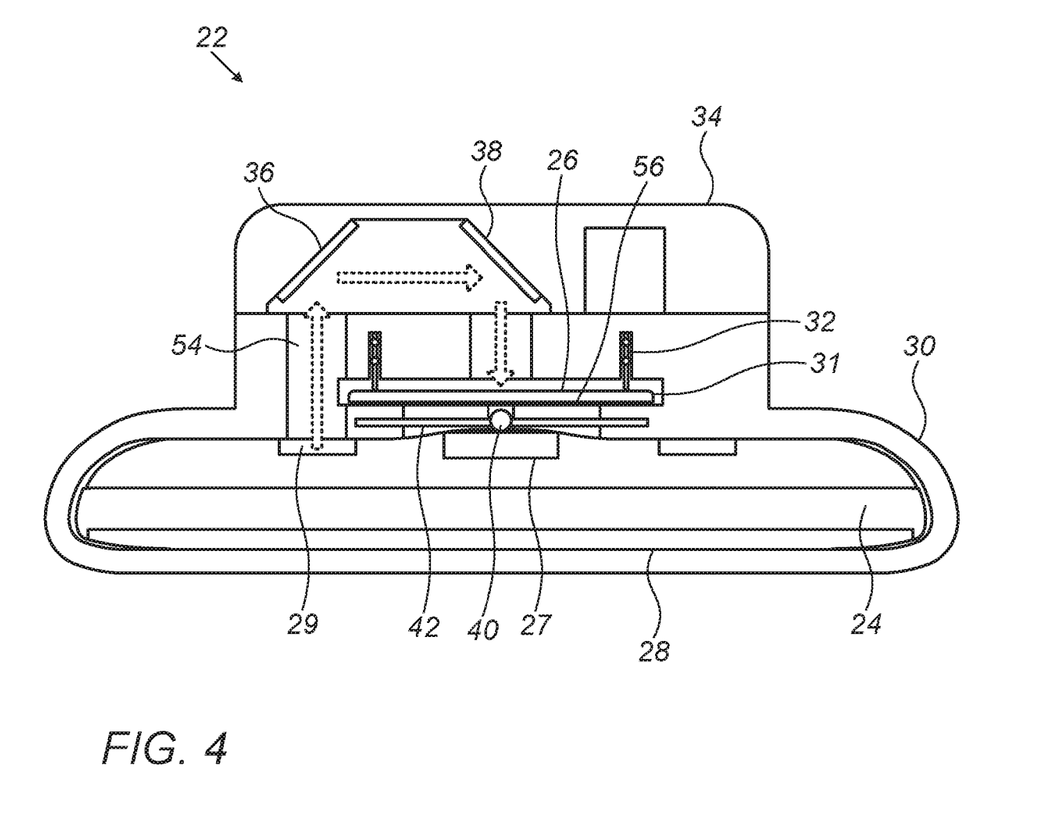
FIG. 4 is a schematic sectional view showing details of the apparatus of FIG. 1, in accordance with an embodiment of the present invention.

FIG. 4 is a schematic sectional view showing details of apparatus 20, and particularly of adapter device 22, in accordance with an embodiment of the present invention. This figure illustrates the functionality of the elements that were described above with reference to FIG. 3. Light source 29 directs a beam 54 of illumination away from the second face of Smartphone 24. Beam 54 is reflected back toward the entrance aperture of camera module 27 in the second face of the Smartphone by the reflective surfaces of mirrors 36 and 38, each of which turns the beam by 90°. In the pictured embodiments, mirrors 36 and 38 comprise front-surface reflectors. Alternatively, one or more reflectors of different design, such as a suitable prism with reflective faces, or even transmissive optics, such as a curved light guide, may be used in place of mirrors 36 and 38.

Following reflection from mirrors 36 and 38, beam 54 back-illuminates a sample 56 held by slide 26. Ball lens 40 creates a magnified image of the sample on the image sensor plane in camera module 27. Smartphone 24 captures and processes the image as described further hereinbelow.

Figure 5:
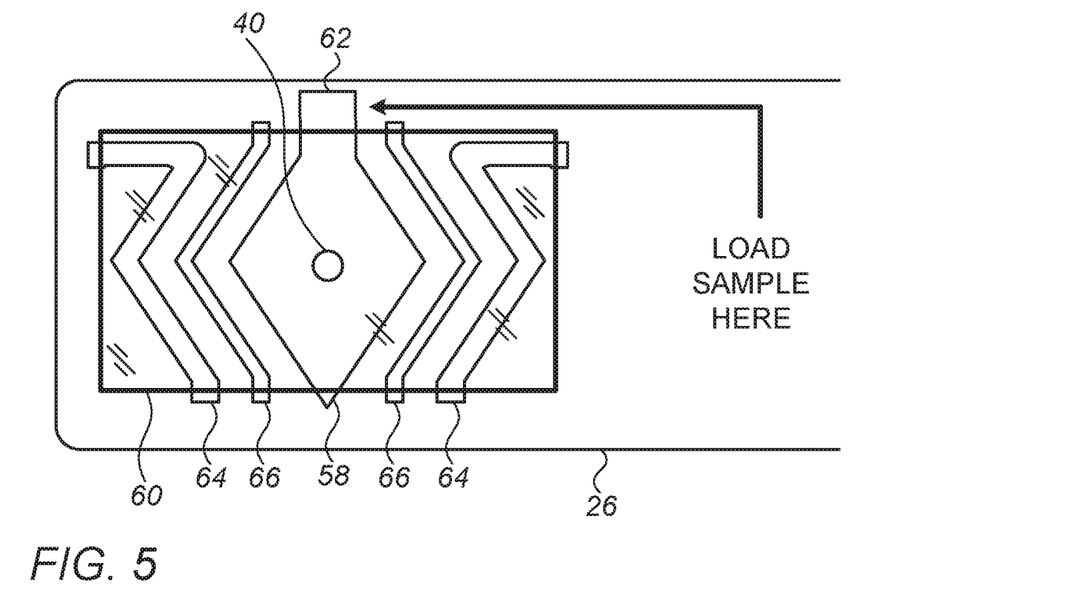
FIG. 5 is a schematic frontal view of a test slide, in accordance with an embodiment of the present invention.

FIG. 5 is a schematic frontal view of test slide 26, in accordance with an embodiment of the present invention. Slide 26 comprises a transparent plastic or glass, which is molded or otherwise manufactured to define a depression 58, typically about 100 µm deep, in the surface of the slide, where the liquid sample is to be held. For example, the depression may alternatively be formed by depositing a layer of a suitable double-sided adhesive, about 100 µm thick, on the surface of the slide around the area that is to hold the sample. A transparent cover slip 60, typically about 0.3 mm thick, is fixed to the slide over the depression (whether molded or formed by double-sided adhesive or other means) so as to define a sample chamber, which is aligned with ball lens 40 as shown in the figure. Cover slip 60 is positioned so as to leave a loading area 62 of depression 58 uncovered. Consequently, when a liquid sample is deposited in loading area 62, the liquid is drawn into the sample chamber by capillary action. Test slide 26 can then be loaded into receptacle 31 for imaging of the sample. The design of test slide 26 ensures that a controlled, known volume of semen will be positioned in the field of view of camera module 27, thus facilitating reliable imaging and assessment.

Typically, cover slip 60 is glued onto slide 26. For this purpose, the slide may be molded to define one or more grooves 64, into which an adhesive is inserted before applying the cover slip to the slide. Once cured (by ultra-violet illumination, for example), the adhesive fixes the cover slip to the slide. To prevent overflow of the adhesive from grooves 64 into the sample chamber, one or more additional grooves 66 may be molded in locations between grooves 64 and depression 58. Alternatively, as noted above, the cover slip may be placed on top of the shaped double-sided adhesive that creates depression 58.

The design of slide 26 and its dimensions are shown and described here by way of example. In alternative embodiments (not shown in the figures), adapter device 22 may accommodate sample holders of other dimensions and designs.

Figure 6:
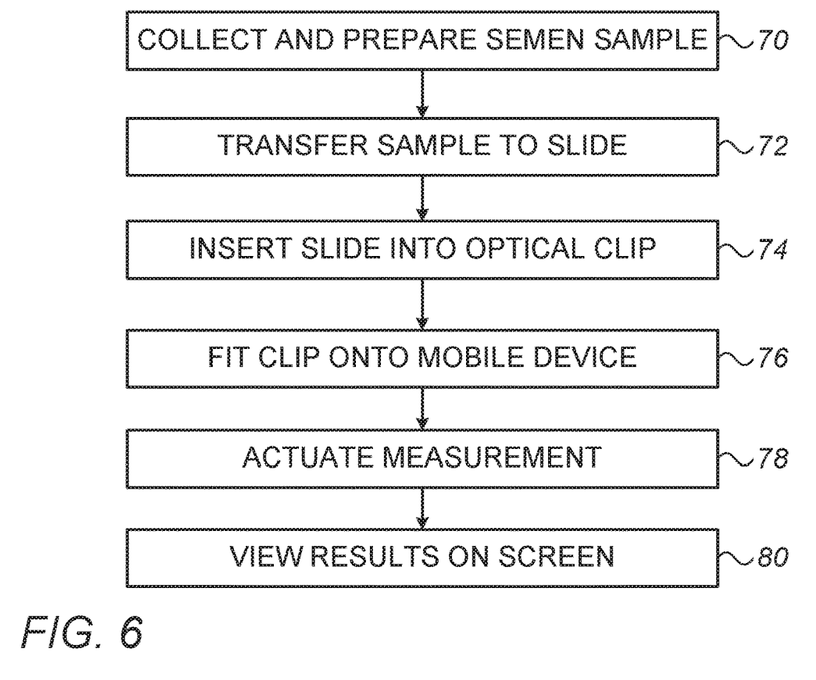
FIG. 6 is a flow chart that schematically illustrates a method for sperm testing, in accordance with an embodiment of the present invention.

FIG. 6 is a flow chart that schematically illustrates a method for sperm testing, in accordance with an embodiment of the present invention. The method is described, for the sake of convenience and clarity, with reference to apparatus 20, but may similarly be applied using mobile computing devices with other sorts of adapters and samples.

The user begins the procedure with the preliminary step of installing testing application software in Smartphone 24. The software may be downloaded from a Web site or "app store," as is known in the art. It includes a user interface, which guides the user in carrying out the test and receives user input as required, as well as drive components to operate camera module 27, light source 29, and display screen 28 as needed. The application software also includes image processing and analysis components, which analyze the images of the sample that are captured by the camera module and compute the test results.

Once the application has been installed, the user collects and prepares a semen sample, at a sample preparation step 70. For this purpose, the user may mix the semen with a liquefying agent, such as chymotrypsin, to reduce its viscosity. The user inserts a small amount of the sample into loading area 62, at a sample transfer step 72, whereupon the sample is drawn into the chamber defined by depression 58, at a sample transfer step 72. For example, the user may draw a small amount of the liquefied semen into a capillary tube, and then place the end of the capillary tube in the loading area so that the semen fills the sample chamber.

The user inserts slide 26 with the sample into receptacle 42 of optical adapter device 22, so that the slide is held firmly in place, at a slide insertion step 74. The user then clips device 22 over the end of Smartphone 24, as shown in the preceding figures, at a device fitting step 76. Alternatively, the order of steps 74 and 76 may be reversed. In either case, the sample is now ready for imaging.

The user indicates to the testing application on Smartphone 24 that the sample is in position by pressing a control presented on screen 28, at a measurement actuation step 78. This step causes the application to turn on light source 29 and operate camera module 27 to capture one or more images of the sample. The image processing component of the application causes the processor in Smartphone 24 to process the electronic images in the mobile computing device so as to compute and output an assessment of the sample. The processing performed at this step is described in greater detail hereinbelow with reference to FIG. 7.

Upon completion of processing the captured images, Smartphone 24 outputs the results, typically via display screen 28, at a data output step 80. The measurement results, such as the MSC, may be output as a numerical value. Alternatively or additionally, it may be preferable simply to report the range in which the result falls, so as to indicate to the user viewing the display whether or not there is cause for concern. For example, in the case of MSC, the result may be reported to the user as "normal" if it is no less than 6 million/ml, or as "low" if the result is below 6 million/ml. In the latter case, the user may be prompted to run the test again, and to see a doctor if the MSC is again found to be low.

Figure 7:
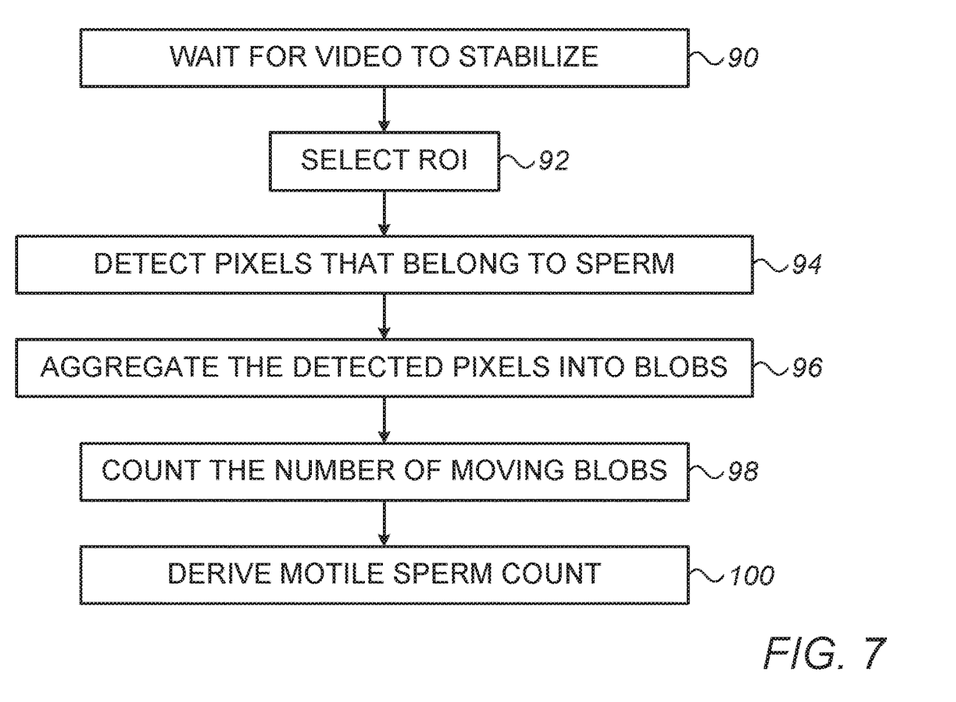
FIG. 7 is a flow chart that schematically illustrates a method for automatic evaluation of motile sperm concentration, in accordance with an embodiment of the present invention.

FIG. 7 is a flow chart that schematically illustrates a method for automatic evaluation of sperm motility, in accordance with an embodiment of the present invention. This method is initiated when the user actuates the measurement process at step 78 (FIG. 6). As noted above, at this step, light source 29 begins to operate, and camera module 27 captures a sequence of images of the backlit sample, typically at a high-resolution setting. Smartphone 24, operating under the control of the above-mentioned application software, waits for the resulting video images to stabilize, at a stabilization step 90. Waiting for stabilization is helpful because the Smartphone auto-focus feature requires time to acquire an optimal video focus while the camera module is running. The Smartphone processor may simply wait for a predefined time, such as 20 seconds, at step 90. Alternatively, the application program may receive feedback from camera module 27 indicating that the auto-focus has locked, and only at that point will it begin capturing images for analysis.

Within the stable video image, the Smartphone processor chooses the area that presents the clearest view of the sperm cells for analysis, at a region of interest (ROI) selection step 92. The inventors have found that an ROI of 700×700 pixels is convenient for analysis and gives reliable results. The processor attempts to select an ROI with good focal quality and contrast. For this purpose, for example, the processor may seek the maximal gradient of gray-level change at every pixel over time (over all processed image frames) and determine the maximum gradient over all the pixels. The processor identifies all pixels in the captured video stream that had a gradient of at least 50% of the maximal gradient at least once in the image sequence. The ROI is then chosen to be the area of 700×700 pixels that is centered at the center of gravity of all of the identified high-gradient pixels.

The application program next causes the Smartphone processor to detect pixels within the ROI that may belong to sperm cells, at a pixel detection step 94. Pixels belonging to sperm cells are defined as dark pixels surrounded by an area of brighter pixels. These dark pixels are detected by first defining the brightness of the background environment and of the areas that are suspected to contain sperm cells, and then this brightness criterion to sort the pixels in the images.

The processor aggregates the potential sperm pixels that it has detected into blobs, at a pixel aggregation step 96. This step may use image processing methods that are known in the art for identification of connected components. Typically, groups of adjoining sperm pixels are labeled to identify them as "blobs," and the blobs are filtered by size, so that only blobs of a certain minimum size are classified as sperm cells. In each image, the processor marks the center of each blob that satisfies these criteria.

The processor counts the number of moving sperm in each image frame by comparing the location of each blob relative to its location in the preceding frame, at a movement counting step 98. If a given blob is found to have moved, the sperm movement count is incremented by one. The total number of blobs that have moved thus gives the movement count for each frame. The processor then computes the motile sperm count based on the median count of moving blobs per image frame, at a motility counting step 100. This value is scaled by the volume of semen contained in the ROI in order to give the actual MSC value, as defined above. The result is output to screen 28 at step 80 (FIG. 6).

Alternatively, other methods of image processing that are known in the art may be applied in analyzing the sequence of images of the sample captured by camera module 27. These alternative methods, as well as the method described above, may be applied not only in computing MSC, but also in extracting measures of sperm count and/or motility alone, as well as analyzing other qualities of semen and other sorts of samples.

Although the embodiments described above refer specifically to sperm testing, and more particularly to assessment of MSC, the principles of the present invention may similarly be applied in testing samples of other sorts, using the capabilities of existing mobile computing devices. It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A sample holder, comprising:
a slide, containing a depression in a surface of the slide; and
a cover slip, which is fixed to the slide over the depression so as to define a sample chamber, while leaving a loading area of the depression uncovered, so that a liquid sample deposited in the loading area is drawn into the sample chamber by capillary action,
wherein the depression is molded into the slide;
wherein the slide is molded to define at least one first groove, into which an adhesive is inserted that fixes the cover slip directly to the slide, and at least one second groove located between the at least one first groove and the depression so as to prevent overflow of the adhesive from the at least one first groove into the sample chamber;
wherein the at least one first groove and the at least one second groove each extend beyond the cover slip on multiple sides of the cover slip.

2. The sample holder according to claim 1, wherein the depression is in a diamond shape where one corner of the diamond is enlarged to form the loading area, wherein the at least one first groove and the at least one second groove each have a V-shaped portion parallel to a side of the depression.

3. The sample holder according to claim 1, wherein the slide is configured to position a predefined volume of the liquid sample in a field of view when the liquid sample is deposited in the loading area.

4. The sample holder according to claim 3, wherein the field of view is the field of view of an imaging device.

5. The sample holder according to claim 4, wherein the imaging device is a camera module of a mobile computing device.

6. The sample holder according to claim 3, wherein the slide is configured for insertion into an optical adapter that fits over a mobile computing device, which includes a camera module configured to capture an image of the liquid sample, and wherein the field of view is the field of view of the camera module when the slide is inserted in the optical adapter and the optical adapter is fitted over the mobile computing device.

7. The sample holder according to claim 6, wherein the liquid sample comprises semen.

8. The sample holder according to claim 1, wherein the slide is configured for insertion into an optical adapter that fits over a mobile computing device, which includes a camera module configured to capture an image of the liquid sample.

9. A sample holder manufacturing method, comprising:
providing a slide, the slide comprising:
a depression molded into a surface of the slide;
at least one first groove; and
at least one second groove located between the at least one first groove and the depression;
inserting an adhesive into the at least one first groove;
contacting the adhesive with the cover slip to fix the cover slip to the slide in a position such that the cover slip defines a sample chamber between the cover slip and the depression while a loading area of the depression is left uncovered and the at least one first groove and the at least one second groove each extend beyond the cover slip on multiple sides of the cover slip.

* * * * *